United States Patent [19]

Petri, Jr. et al.

[11] Patent Number: 5,401,831
[45] Date of Patent: Mar. 28, 1995

[54] MONOCLONAL ANTIBODIES FOR DIFFERENTIATING PATHOGENIC AND NONPATHOGENIC E. HISTOLYTICA

[75] Inventors: William A. Petri, Jr., Glen Allen; Jonathan I. Ravdin, Earlysville, both of Va.

[73] Assignee: University of Virginia Patents Foundation, Charlottesville, Va.

[21] Appl. No.: 75,226

[22] Filed: Jun. 10, 1993

Related U.S. Application Data

[62] Division of Ser. No. 479,691, Feb. 13, 1990, Pat. No. 5,272,058.

[51] Int. Cl.$^6$ .................. C07K 15/28; G01N 33/569
[52] U.S. Cl. ........................ 530/388.6; 435/7.22; 435/240.27; 530/822
[58] Field of Search ............ 530/388.2, 388.6, 822; 935/89, 103, 104, 106, 107; 435/240.26, 7.22; 424/240.27, 85.8

[56] References Cited

U.S. PATENT DOCUMENTS

| | | | |
|---|---|---|---|
| 5,004,608 | 4/1991 | Ravdin et al. | 424/88 |
| 5,272,058 | 12/1993 | Petri et al. | 435/7.22 |

OTHER PUBLICATIONS

Kohler et al (1975) "Continuous cultures of fused cells . . . " Nature 256:495–497.
Petri et al (1987) "Recognition of the Galactose-. . . " Infect. & Immun. 55:2327–2331.
Ravdin et al., "Relationship of Free Intracellular Calcium to the Cytolytic Activity of *Entamoeba histolytica*", *Infect. Immun.* 56:1505–1512 (1988).

*Primary Examiner*—Carol E. Bidwell
*Attorney, Agent, or Firm*—Morrison & Foerster

[57] ABSTRACT

A method to prepare a monoclonal antibody (mAb) specifically immunoreactive with an epitope of the Gal/GalNAc lectin of a pathogenic or nonpathogenic *E. histolytica*, or the 70 kd subunit thereof, is provided. This method comprises culturing an immortalized cell line capable of secreting the mAbs, where the cell line is obtained by immortalizing antibody-producing cells from a mammal immunized with a purified 170 kd subunit, or with purified Gal/GalNAc lectin of a pathogenic *E. histolytica*. The supernatants of the cells are screened for the presence or absence of antibodies specific for the subunit or lectin from a pathogenic *E. histolytica* and from a pathogenic *E. histolytica*, so as to determine the pathogen/nonpathogen specificity of the monoclonal antibody. Antibodies produced by this method and epitopes with which they react on pathogenic and/or nonpathogenic *E. histolytica* also are disclosed.

5 Claims, 2 Drawing Sheets

MONOCLONAL ANTIBODIES FOR DIFFERENTIATING PATHOGENIC AND NONPATHOGENIC E. HISTOLYTICA

This invention was made with Government support under Contract AI 18841 awarded by the National Institute of Health. The Government has certain rights in the invention.

This application is a division of application Ser. No. 07/479,691, filed, Feb. 13, 1990, now U.S. Pat. No. 5,272,058.

TECHNICAL FIELD

The invention relates to diagnosis of parasitic diseases. More particularly, the invention offers a method to diagnose infection with *Entamoeba histolytica* and to distinguish pathogenic from nonpathogenic strains.

BACKGROUND ART

*Entamoeba histolytica* infection is extremely common and affects an estimated 480 million individuals annually. However, only about 10% of these persons develop symptoms such as colitis or liver abscess. The low incidence of symptom occurrence is putatively due to the existence of both pathogenic and nonpathogenic forms of the amoeba. As of 1988, it had been established that the subjects who eventually exhibit symptoms harbor "zymodemes" which have been classified as such on the basis of their distinctive hexokinase and phosphoglucomutase isoenzymes. The pathogenic forms are not, however, conveniently distinguishable from the nonpathogenic counterparts using morphogenic criteria.

The distinction between pathogenic and nonpathogenic strains in diagnosis is of great practical importance, because only persons infected with *E. histolytica* who will develop the disease should be treated. This is bad enough in developed countries where it would at least be possible economically to treat every carrier with a known effective drug (metronidazole); it is, of course, undesirable to administer such drugs unnecessarily. In less developed countries the cost of these unnecessary administrations is significant enough to have a dramatic negative impact on the resources for overall health care.

There is an almost perfect correlation between infection with a pathogenic zymodeme and development of symptoms and between infection with a nonpathogenic zymodeme and failure to develop these symptoms. As a general proposition, only pathogenic strains can be grown axenically (i.e., in the absence of an associated microorganism) and nonpathogenic strains have been made to grow in this manner only by "training" them to do so in a series of media alterations beginning with attenuated bacteria. The adaptation was accompanied by exhibition of the enzyme pattern characteristic of pathogenic strains (Mirelman, D., et al., *Infect Immun* (1986) 54:827–832). This work has not been repeatable in other laboratories, and more recent work on genomic differences (see below) indicates that the pathogenic and nonpathogenic forms are separate species.

It is known that *E. histolytica* infection is mediated at least in part by the "Gal/GalNAc" adherence lectin which was isolated from a pathogenic strain and purified 500 fold by Petri, W. A., et al., *J Biol Chem* (1989) 264:3007–3012. This successful isolation and purification was preceded by the production of mouse monoclonal antibodies which inhibit the in vitro adherence of the amoebic trophozoites; the antibodies were prepared from immortalized cells from spleens of mice immunized with sonicated trophozoites grown in axenic culture after having originally been isolated as a pathogenic strain from an affected subject. (Ravdin, J. I., et al., *Infect Immun* (1986) 53:1–5.) The cells were screened by the ability of the supernatants to inhibit adherence of the trophozoites to target tissue. All of these reported monoclonal antibodies, therefore, are presumably immunoreactive with the Gal/GalNAc surface adhesin of the pathogen. The Gal/GalNAc lectin was then prepared by galactose-affinity chromatography and reported in 1987. (Petri, W. J., et al., *J Clin Invest* (1987) 80:1238–1244). Studies of serological cross-reactivity among patients having symptomology characteristic of *E. histolytica* pathogenic infection, including liver abscess and colitis, showed that the adherence lectin was recognized by all patients' sera tested (Petri, Jr., W. A., et al., *Am J Med Sci* (1989) 296:163–165).

The purified "Gal/GalNAc" lectin was shown to have a nonreduced molecular weight of 260 kd on SDS-PAGE. After reduction, with beta-mercaptoethanol, the lectin separated into two subunits of 170 and 35 kd MW. Further studies showed that antibodies directed to the 170 kd subunit were capable of blocking surface adhesion to test cells, and therefore, the 170 kd subunit is believed to be of primary importance in mediating adhesion.

Despite the generally interesting and useful results cited above, the ability to diagnose the presence or absence of pathogenic strains of *E. histolytica* has proved difficult. Since both pathogens and nonpathogens are morphologically similar, microscopic tests are not particularly useful. ELISA techniques have been used to detect the presence or absence of *E. histolytica* antigen in both stool specimens and in sera, but these tests do not seem to distinguish between the pathogenic and nonpathogenic strains. Root et al., *Arch Invest Med* (Mex) (1978) 9: Supplement 1:203, pioneered the use of ELISA techniques for the detection of amoebic antigen in stool specimens using rabbit polyclonal antiserum. Various forms of this procedure have been used since, some in correlation with microscopic studies, and all using polyclonal antisera. None of these, apparently, pinpoints the instances of infection with the pathogenic as opposed to nonpathogenic form. See, for example, Palacios et al., *Arch Invest Med* (Mex) (1978) 9: Supplement 1:203; Randall et al., *Trans Roy Soc Trop Med Hyg* (1984) 78:593; Grundy, *Trans Roy Soc Trop Med Hyg* (1982) 76:396; Ungar, *Am J Trop Med Hyg* (1985) 34:465.

These studies on stool specimens are summarized in *Amebiasis: Human Infection by Entamoeba Histolytica*, J. Ravdin, ed. (1988) Wiley Medical Publishing, pp. 646–648. Similar methods to detect characteristic *E. histolytica* antigens in serum and in liver abscess fluid are equally unable to distinguish pathogens from nonpathogens (ibid., pp. 661–663). As summarized in this article, as of 1988, the only known way to distinguish pathogenic from nonpathogenic forms of this amoeba was through characterizing the isoenzyme pattern using electrophoresis.

Recently it has been shown by two different groups that differences between pathogenic and nonpathogenic strains can be demonstrated using comparisons of DNA isolates. Garfinkel, L. I., et al., *Infect Immun* (1989) 57:926–931 developed DNA probes which hybridize to DNA isolated from *E. histolytica* and four types of restriction fragment length patterns were obtained. These patterns correlated with pathogenic/nonpathogenic distinctions. Similarly, Tannich, E., et al., *Proc Natl Acad Sci* (1989) 86:5118–5122 probed cDNA libraries constructed from various strains and showed that pathogenic isolates were genetically distinct from nonpathogenic ones. However, these techniques require the culture of the organisms isolated from patients to obtain sufficient quantities for testing, and are thus time consuming and labor intensive.

Strachan, W. D., et al., *Lancet* (1988) 561–562, report the production of two monoclonal antibodies designated 22.3 and 22.5 which were members of a large group prepared by standard procedures from mice immunized with axenic cultures of a pathogenic *E. histolytica* strain NIH200/ATCC 30458. These monoclonal antibodies were tested in an immunofluorescence assay with cultures obtained from both putatively invasive and noninvasive strains, and appeared to immunoreact only with culture samples of invasive strains. There is no indication in this publication as to the manner of screening for antibodies with this characteristic, it is not known to what target these antibodies bond, nor would it be possible, without these specific antibodies, to reproduce this result. The test described requires intact *E. histolytica* and therefore cannot be applied in serum, urine or liver abscess fluid and can only be applied to stool samples which are freshly collected.

It would be highly desirable to have a relatively simple clinical test which would detect the presence of *E. histoytica* antigen in samples taken from patients and to be able to distinguish whether these antigens are associated with pathogenic or nonpathogenic strains. The present invention offers such a test, by employing conventional immunoassay procedures using monoclonal antibody reagents which are specifically immunoreactive with pathogenic and/or nonpathogenic Gal/GalNAc adherence lectin.

DISCLOSURE OF THE INVENTION

The invention provides a simple diagnostic test which permits the assessment of patients for invasive *E. histolytica* infection. The test comprises the use, in an immunoassay, of monoclonal antibodies which are specific to certain of the various epitopic domains of the 170 kd subunit of the adherence lectin. These antibodies are obtained by mapping of the *E. histolytica* adherence lectin epitope pattern and correlating the reactivity with pathogenic and nonpathogenic strains. By conducting suitable controlled immunoassays, therefore, a diagnosis for the presence of *E. histolytica* combined with a determination of pathogenicity or nonpathogenicity can be performed.

Thus, in one aspect, the invention is directed to a method to detect the presence or absence of pathogenic *E. histolytica* in patients, which method comprises contacting a biological sample obtained from said patients with a monoclonal antibody preparation which specifically immunoreacts with an epitope characteristic of the pathogenic form of the 170 kd subunit of the Gal/GalNAc adherence lectin to form a complex in the presence of the pathogenic infection and detecting the presence or absence of the complex. In another aspect, the invention is directed to detect the presence or absence of nonpathogenic *E. histolytica* in a subject using a similar procedure but substituting an antibody preparation which specifically immunoreacts with the nonpathogenic form of the adherence lectin. The assay can also be adapted to detect the presence or absence of *E. histolytica* in general using antibodies directed to epitopes which are common to both pathogenic and nonpathogenic strains. A particularly preferred form of the invention method involves combining detection of *E. histolytica* in general with detection of the pathogenic form. The invention also includes kits for the conduct of the method.

In still another aspect, the invention is directed to purified forms of the Gal/GalNAc lectin and its 170 kd subunit of either pathogenic or nonpathogenic *E. histolytica*, to methods for their preparation and to monoclonal antibodies specifically immunoreactive with the epitopes unique to the nonpathogenic subunit and to methods for their preparation. In still another aspect, the invention is directed to monoclonal antibodies immunoreactive with epitopes 1–3 of 170 kd subunits of either pathogenic or nonpathogenic *E. histoytica*.

The invention also is directed to serological tests for the detection of antibodies reactive with pathogenic or nonpathogenic forms of *E. histolytica*, and to kits for conducting them.

The monoclonal antibodies illustrated hereinbelow have been shown either to be pathogenic or nonpathogenic form-specific or to immunoreact with epitopes common to all types of *E. histolytica* 170 kd subunit Gal/GalNAc lectin. Additional candidate antibodies can be classified with respect to their specificity by assessing their cross-reactivity in immunoassays with the monoclonal antibodies described below.

MODES OF CARRYING OUT THE INVENTION

Figure 1:
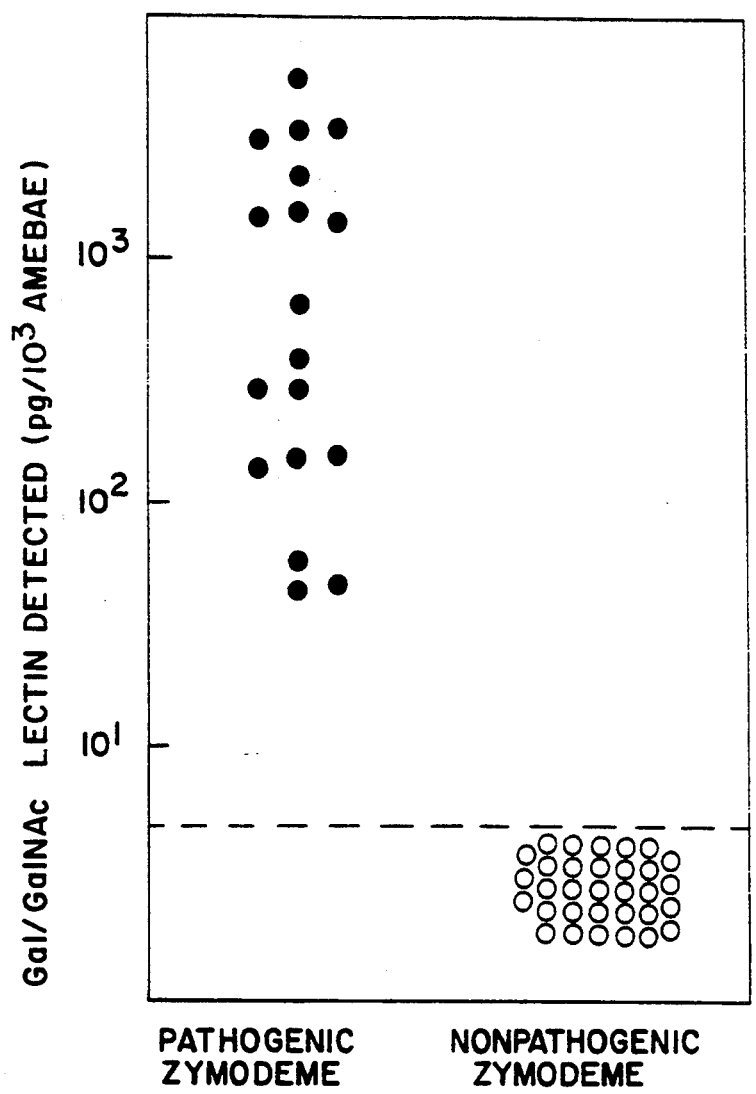
FIG. 1 shows the correlation of reactivity with mAb-recognizing epitope 3 of the 170 kd subunit with pathogenic/nonpathogenic forms.

The present invention provides a method to obtain antibodies which are immunospecific for an epitope of the 170 kd subunit of the Gal/GalNAc adherence lectin of the form which occurs in pathogenic forms of *E. histolytica*, but which does not occur in nonpathogenic forms. Antibodies with this specificity, which can now be conveniently prepared by this method, are useful in simple immunoassays to detect the presence or absence of pathogenic strains of *E. histolytica* in biological samples, and to distinguish them from nonpathogenic forms. These antibodies are monoclonal preparations which are obtainable by immortalizing antibody-producing cells from mammals immunized with purified 170 kd subunit of the Gal/GalNAc lectin from pathogenic *E. histolytica*.

Similarly, antibodies which are specifically immunoreactive with nonpathogenic forms of this lectin can be prepared by immortalization of antibody-secreting cells from a mammal immunized with purified 170 kd subunit of this lectin isolated from nonpathogenic forms. The antibodies provided herein permit convenient purification of these nonpathogenic lectins. Additional mAbs which recognize the 170 kd subunit of both pathogenic and nonpathogenic forms are also prepared.

Definitions

As used herein, "immunospecific" with respect to a specified target means that the antibody thus described binds that target with significantly higher affinity than that with which it binds to alternate haptens. The degree of specificity required may vary with circumstances, but typically an antibody immunospecific for a designated target will bind to that target with an affinity which is at least one or two, or preferably several orders of magnitude greater than that with which it binds alternate haptens.

Furthermore, as used herein, the term "antibody" refers not only to immunoglobulins per se, but also to fragments of immunoglobulins which retain the immunospecificity of the complete molecule. Examples of such fragments are well known in the art, and include, for example, Fab, Fab', and F(ab')$_2$ fragments. The term "antibody" also includes not only native forms of immunoglobulins, but forms of the immunoglobulins which have been modified, as techniques become available in the art, to confer desired properties without altering the immunospecificity. For example, the formation of chimeric antibodies derived from two species is becoming more practical. In short, "antibodies" refers to any component of or derived form of an immunoglobulin which retains the immunospecificity of the immunoglobulin per se.

The term "pathogenic forms" of E. histolytica refers to those forms which are invasive and which result in symptomology in infected subjects. "Nonpathogenic forms" refer to those forms which may be harbored asymptomatically by carriers.

"Gal/GalNAc lectin" refers to a glycoprotein found on the surface of E. histolytica which mediates the adherence of the amoeba to target cells, and which mediation is inhibited by galactose or N-acetylgalactosamine. The Gal/GalNAc lectin refers specifically to the lectin reported and isolated by Petri et al. (supra) from the pathogenic strain HMI-IMSS, and to the corresponding lectin found in other species of E. histolytica. The "170 kd subunit" refers to the large subunit obtained by Petri et al. upon reduction of the Gal/GalNAc lectin and its corresponding counterparts in other species.

The "antibodies" of the invention, as defined above, are immunospecific for the 170 kd subunit of the Gal/GalNAc lectin associated with Entamoeba histolytica. Three categories of such antibodies are prepared. One category of antibody is immunospecific for epitopes which are found on the 170 kd subunit of Gal/GalNAc lectin which are "unique" to pathogenic forms. These antibodies are capable, therefore, of immunoreaction to a significant extent only with the pathogenic forms of the amoeba or to the 170 kd subunit of lectin isolated from pathogenic forms. Conversely, a second set of antibodies is immunoreactive with epitopes which are "unique" to the 170 kd subunit of Gal/GalNAc lectin which is found in nonpathogenic forms. Thus, these antibodies are immunoreactive to a substantial degree only with the nonpathogenic amoeba or their lectins and not to the pathogenic forms. Finally, a third category of antibodies is immunoreactive specifically with epitopes common to pathogenic and nonpathogenic forms and contained in the 170 kd subunit of the Gal/GalNAc lectin. These antibodies are capable of immunoreaction with the subunit or with the amoeba regardless of pathogenicity.

With respect to the illustrative antibodies prepared herein, those immunoreactive with epitopes 1 and 2 of the 170 kd subunit isolated from the pathogenic strain exemplified are capable of reacting, also, with the corresponding epitopes on nonpathogens. On the other hand, those immunoreactive with epitopes 3-6 are capable of immunoreaction only with the 170 kd subunit of pathogenic strains. By applying the invention techniques for isolation of the 170 kd subunit to amoeba which are nonpathogenic, a 170 kd subunit can be obtained for immunization protocols which permit the analogous preparation of mAbs immunoreactive with counterpart epitopes 3-6 in the nonpathogenic forms.

The monoclonal antibodies reported in the art, as set forth in the Background section above, were prepared using a screening procedure which screens for inhibition of an adherence of the amoeba to target cells. Therefore, the prior art antibodies are distinct from those which bind to epitopes 1, 2 and 3, which are shown hereinbelow either to enhance or to have no effect on the binding of the amoeba to target cells or proteins. Accordingly, those antibodies which immunoreact with epitopes 1, 2 and 3 are not available in the art.

The monoclonal antibodies of the invention are prepared by culturing immortalized cell lines which are capable of secreting them. The culturing of these lines is generally done in two ways-through in vitro culture methods with nutrients as generally understood, or by injection into suitable hosts, such as mice, in order to permit proliferation in vivo, with subsequent recovery of the mAbs from ascites fluid. As used herein, "culturing" an immortalized cell line and "recovering the mAbs from the culture" includes the procedures using both of these approaches.

Preparation of Purified Gal/GalNAc Lectin

The preparation of a highly purified form of the Gal/GalNAc lectin derived from a pathogen of E. histolytica is described in detail in Example 1. The preparation comprises an affinity chromatography step wherein monoclonal antibodies immunospecific to the 170 kd subunit of the reduced form of the Gal/GalNAc lectin are used as an affinity ligand to isolate the lectin from a solubilized preparation of the amoeba. The isolated lectin can be then reduced using standard methods, such as contact with a sulfhydryl reducing agent, for example dithiothreitol or beta-mercaptoethanol, to obtain the 170 kd subunit which is significant in mediating adhesion. Either the isolated 170 kd subunit or the purified lectin itself may be used for immunization to obtain antibody preparations, and in serological testing.

In a manner similar to that set forth in Example 1 as applied to purification of the Gal/GalNAc lectin from pathogenic strains, nonpathogenic lectin may also be purified to a similar level of purity by employing as affinity ligands in the affinity chromatography step monoclonal antibodies which are immunospecific for epitopes which are shared by both pathogenic and nonpathogenic forms. Two such monoclonal preparations are prepared as illustrations herein-those immunoreactive with epitope 1 and those immunoreactive with epitope 2. By use of these monoclonal antibody preparations as affinity ligands, the purified Gal/GalNAc lectin from either pathogenic or nonpathogenic forms may be prepared.

Preparation of Monoclonal Antibodies

Monoclonal antibodies useful in the immunoassays described herein may conveniently be prepared by immunization protocols using the isolated and purified Gal/GalNAc lectins of the invention or the 170 kd subunits obtained by reduction thereof. Use of these lectins in purified and isolated form as immunogens, as well as their availability for use in screening the monoclonal preparations obtained greatly facilitates the preparation and identification of suitable monoclonal antibodies.

For immunization, standard protocols are employed, and any suitable vertebrate, typically a mammal, such as rats, mice, rabbits, and the like, can be used as the subject. When sufficient titers are obtained, the antibody-producing cells of the subject, preferably spleen cells, are subjected to immortalization protocols, most conveniently those for the formation of hybridomas as set forth originally by Kohler and Millstein. However, additional techniques for immortalization such as viral infection may also be used.

The immortalized cells are then screened for the production of the desired mAbs. Generally, the supernatants of the cultured immortalized cells are tested in standard immunoassays, such as ELISA or RIA, which employ as antigen the purified lectin or subunit used as an immunogen. Positively reacting supernatants are then further tested. It is convenient to verify immunoreactivity with the 170 kd subunit by using, as antigen in the assay or in Western blots, the reduced form of the isolated lectin.

The supernatants are then tested for cross-reactivity with the alternate forms of the lectin or subunit. For example, supernatants of antibody-secreting cells prepared from subjects immunized by pathogenic *E. histolytica* are tested by immunoassay against the purified lectin, or other lectin-containing antigen composition of nonpathogenic amoeba. Conversely, supernatants of antibody-secreting cells of subjects immunized with the lectin from nonpathogenic forms are checked-for cross-reactivity with the lectin or other antigen-containing composition derived from the pathogenic alternatives.

Thus, monoclonal antibody preparations are obtained which are either immunoreactive with epitopes shared by both pathogens and nonpathogens, or with epitopes which are unique to the form from which they are derived.

The Assay

For the conduct of the assay of the invention, samples are prepared and any amoebae contained therein solubilized according to standard procedures for the type of sample provided. Stool samples are treated as described, for example, by Ungar, et al., *Am J Trop Med Hyg* (1985) 34:465. Serum or plasma samples are diluted serially in phosphate buffered saline. Stool, serum or plasma samples are preferred, although other biological fluids or biopsy materials can also be used.

The amoebae are solubilized using known techniques for solubilization of the Gal/GalNAc lectin by incubation in a solubilization buffer of appropriate salt concentration and a small quantity of detergent. Typical buffer conditions are approximately 0.1–0.3M total salt, and 0.2–1% detergent, and advantageously include a chelator such as EDTA and a protease inhibitor such as phenylmethylsulfonyl fluoride. The samples are incubated with the solubilization buffer for a time sufficient to effect solution of the lectin, usually about 0.5 hours, and then the solubilized material is recovered by any suitable means, typically by centrifugation.

The samples containing solubilized lectin can then be used directly in the immunoassay. The presence or absence of the pathogenic or nonpathogenic forms of the amoeba can be detected using any standard immunoassay procedure with antibodies of specificity for the 170 kd subunit-with appropriate immunospecificity for epitopes unique to pathogens or nonpathogens or to shared epitopes as described herein.

An essential element of assessment for the presence of pathogenic strains per se, is the contacting of the prepared sample with a monoclonal antibody specific for an epitope unique to the 170 kd subunit of pathogenic amoeba to form a complex in the presence of such pathogens and detection of the formation of the complex; an analogous procedure applies with respect to detection of nonpathogens wherein a monoclonal antibody specific for an epitope unique to the nonpathogenic 170 kd subunit is used. In a preferred approach, however, the sample is assayed in a sandwich-type protocol in which a capture antibody and a detection antibody are used. The capture antibody should preferably bind to a different epitope than the detection antibody.

A preferred form of capture antibody is that binding to epitope 1, and in particular 3F4, ATCC HB10359 which has superior binding capabilities. This mAb binds to an epitope shared by both pathogenic and nonpathogenic forms so that both forms will be captured in the initial step. Typically, this assay is conducted on a solid support which is coated with the capture antibody, suitably blocked, and then treated with the sample containing solubilized lectin according to routine protocols. If the 3F4 is used as a capture antibody, samples containing both nonpathogenic and pathogenic *E. histolytica* will form complexes on the support. The formation of these complexes is then detected, preferably by the use of a detection antibody which is capable of distinguishing between pathogenic and nonpathogenic forms. Suitable detection antibodies for pathogenic forms include those which bind to epitopes 3–6 of the pathogenic subunit; the corresponding antibodies which bind to similar regions of the nonpathogenic subunit are used for the detection of nonpathogens. The formation of the ternary complex is then detected either by a label directly associated with the detecting reagent or by a subsequent reaction with label, such as a suitable antispecies immunoglobulin which is conjugated to label.

Any convenient labeling method may be used, including the use of radioisotopes such as 125-I, 32-P, and the like, or fluorescent labels such as fluorescein or dansyl moieties. Particularly preferred is the use of enzyme label wherein the enzyme such as alkaline phosphatase, horseradish peroxidase or urease is capable of effecting a detectable reaction in a subsequently added substrate solution. Other detection methods involve biotin/avidin labeling or use of gold conjugates. All of these techniques are well known in the art, reagents are available commercially, e.g., from Sigma Chemical Co., St. Louis, Mo., and are applied in a standard fashion.

The invention further includes kits useful for performing the diagnostic assays of the invention. These kits include, in conveniently packaged form, at least a monoclonal antibody composition formulated as a reagent for conduct of the assay. Kits designed for the detection of pathogenic strains will contain at least one monoclonal antibody reagent which is specific for epitopes unique to the Gal/GalNAc lectin of the pathogens; kits designed for detection of nonpathogens specifically similarly will contain at least a reagent containing monoclonal antibodies immunospecific for an epitope unique to the nonpathogenic forms of Gal/GalNAc lectin. Kits designed for detection of *E. histolytica* infection in general, when either form is to be detected, will either contain at least one reagent containing mAb immunospecific for an epitope of Gal/GalNAc lectin which is shared by both pathogens and nonpathogens, or will contain more than one reagent wherein at least one reagent is present which reacts with pathogenic Gal/GalNAc lectin and one reagent is present which reacts with Gal/GalNAc lectin from nonpathogenic forms.

In addition to the required specific immunoreagents, the kits will contain additional reagents required depending on the design of the assay. If the assay is to be conducted on a solid support, the kits may contain both Capture and detection antibodies. In any event, reagents which permit the labeling of the complex formed by the Gal/GalNAc lectin in the sample to be detected and the monoclonal antibody responsible for the desired specificity will also be included. Instructions will also be included for the conduct of the assay.

Serology

The availability of the purified and isolated forms of the Gal/GalNAc lectins of both pathogenic and nonpathogenic *E. histolytica*, and the 170 kd subunits thereof make possible the convenient conduct of serology on patients or other subjects suspected of having positive antibody titers with respect to the pathogenic and/or nonpathogenic forms. The lectin is known to be antigenic in humans (Petri, W. S., et al., *Am J Med Sci* (1989) 296: 163-165).

In a simple test, the purified lectins per se can be used to detect the presence or absence of such antibodies; in a more complex form of the method, the biological fluid may be used as a competition reagent with regard to the binding of monoclonal antibodies known to be specific to pathogenic or nonpathogenic forms and to their relevant lectins.

Thus, in one embodiment, the biological fluid to be tested is contacted with the purified lectin or subunit, which lectin or subunit is derived either from a pathogenic or nonpathogenic form of *E. histolytica* so that a complex is formed. The complex is then detected by suitable labeling either by supplying the antigen in labeled form or by a secondary labeling process which forms a ternary complex. The reaction is preferably conducted using a solid phase to detect the formation of the complex attached to solid support, or the complex can be precipitated using conventional precipitating agents such as polyethylene glycol.

In a more complex form of the assay, competitive assays, analogous to those used in the epitope mapping studies of example 2 herein, can be used wherein the biological fluid, preferably serum or plasma, provides the cold antibody to compete with a labeled monoclonal antibody preparation known to bind specifically to an epitope unique to the Gal/GalNAc lectin or its 170 kd subunit of a pathogenic or nonpathogenic form. In this embodiment, the binding to labeled specific monoclonal antibody is conducted in the presence and absence of biological fluid, and the diminution of labeling of the resulting complex in the presence of fluid is used as an index to determine the level of competing antibody.

Kits suitable for the conduct of these methods include the appropriate labeled antigen or antibody reagents and instructions for conducting the test.

The following examples are intended to illustrate but not to limit the invention:

EXAMPLE 1

Preparation of Monoclonal Antibodies Immunoreactive With the 170 kd Subunit

A. mAbs reactive with pathogenic-unique and pathogenic/nonpathogenic shared epitopes.

Axenic *E. histolytica*, pathogenic strain HMI-IMSS were grown in medium TYIS-33 (trypticase yeast extract, iron and serum) with 100 U/ml penicillin and 100 mg/ml streptomycin sulfate at 37° C. in 250 ml plastic tissue culture flasks. The amoebae were harvested after 72 hours of growth by centrifugation at $150 \times g$ for 5 min at 4° C. and washed twice in ice cold 75 mM Tris, 65 mM NaCl, pH 7.2.

The trophozoites harvested from four 250 ml flasks were preincubated on ice in 5 ml of 75 mM Tris, 65 mM NaCl with a 1:1000 dilution of diisopropylfluorophosphate before solubilization in 10 ml of 150 mM NaCl, 50 mM Tris, pH 8.3, 0.5% Nonidet P-40, 5 mM EDTA and 2 mM phenylmethylsulfonyl fluoride. The solubilized amoebae were microfuged for 10 min and the supernatant was applied at 4° C. to a monoclonal antibody affinity column consisting of 2 mg each of protein A-purified anti-lectin monoclonal antibodies H85, 7F4, 5B8, 3F4 and 6D2 immobilized on 1-2 ml of Affi-Gel 10. This purification method and these antibodies are described in Petri, Jr., W. A., et al., *J Biol Chem* (1989) 264:3007-3012 (supra), incorporated herein by reference. The supernatant was recirculated through the column with a peristaltic pump overnight, and the column was then washed with 15 ml of solubilization buffer followed with 15 ml of phosphate-buffered saline, pH 7.5.

The bound lectin was eluted with 10 ml of 0.2N acetic acid, pH 2.5; immediately neutralized by collecting eluted fractions into a 50 ml tube containing 5 ml of 1.5M Tris, pH 8.8; dialyzed overnight against distilled water, frozen and lyophilized.

The purified lectin was used for immunization and the immunized mice spleen cells used for fusions to produce hybridomas as previously described in detail in Petri, Jr., W. A., et al., *J Clin Invest* (1987) 80:1238; Petri, Jr., W. A., et al., *J Biol Chem* (1989) 264:3007; and Ravdin, J. I., et al., *Infect Immun* (1986) 53:1, all cited above and all incorporated herein by reference. The monoclonal antibodies were obtained from two fusions using spleen cells from BALB/c mice injected with purified lectin in complete and then in incomplete Freund's adjuvant followed by a final boost intrasplenically. The supernatants were assayed by standard ELISA using the lectin-coated (1 mg/well) microtiter plates and 36 positively-testing supernatants were obtained. The positive supernatants were then tested for immunoreactivity with the 170 kd lectin subunit by Western blot and 10 of the 36 were positive in this assay.

These 10 monoclonal antibodies were isotyped and purified from 50% ammonium sulfate fractions of ascites by preparative isoelectric focusing or protein A affinity chromatography as described by Chapman, M. D., et al., *J Immunol* (1987) 139:1479. The monoclonal antibodies were labeled with I using the chloramine T technique to a specific activity of 20-40 uCi/ug according to the method of Klinman, N. R., et al., *Clin Exp Immunol* (1969) 4:473.

B. mAbs reactive with nonpathogenic-unique and pathogenic/nonpathogenic shared epitopes.

Figure 2:
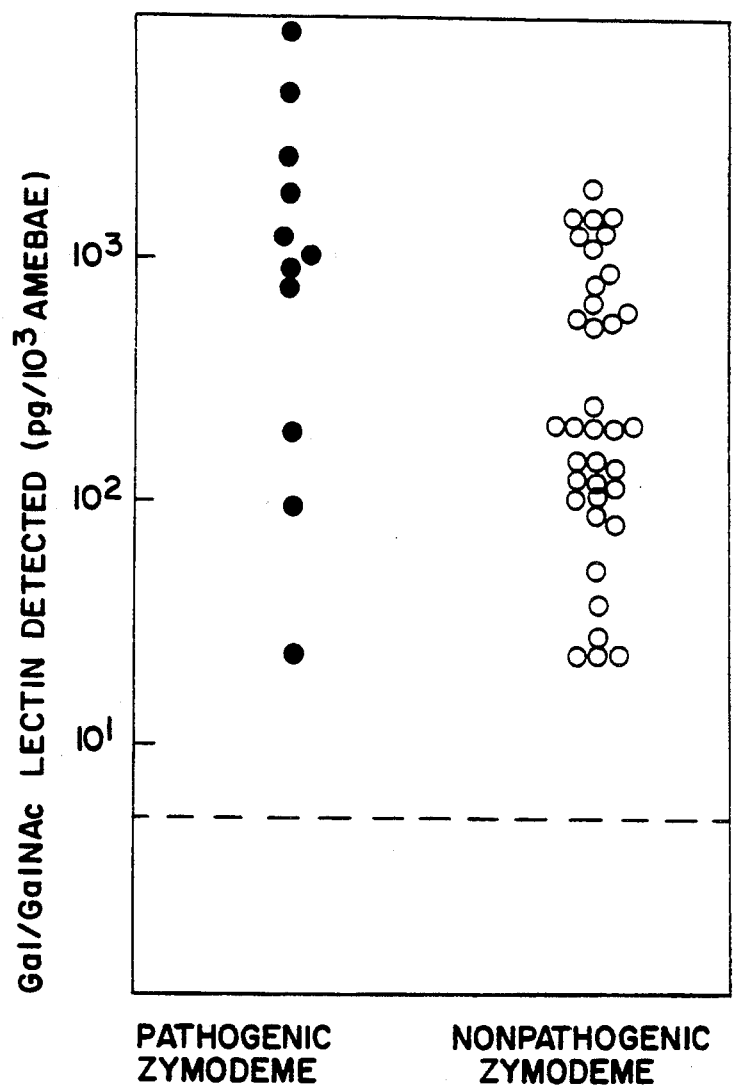
FIG. 2 shows the correlation of reactivity with mAb which recognizes epitope 2 of the 170 kd subunit with pathogenic/nonpathogenic forms.

In a manner similar to that set forth in paragraph A herein above, the purified form of the Gal/GalNAc lectin associated with nonpathogenic forms of *E. histolytica* is isolated and used in immunization protocols. Suitable mAbs useful in affinity chromatography include those directed to epitopes 1 and 2 of the 170 kd subunit (see below). The immortalized cells obtained from immunized mammals are then, in an analogous manner, screened for immunoreactivity using an ELISA assay employing microtiter plates coated with the purified nonpathogenic lectin. Reactivity with the 170 kd subunit is confirmed by Western Blot as described in paragraph A. Monoclonal antibodies capable of reacting with the 170 kd subunit are then isotyped and purified as described in paragraph A.

EXAMPLE 2

Classification of mAb by Epitope Specificity

A. The epitope specificity of the 10 mAbs of paragraph A, Example 1, was sorted by cross-inhibition RIA using $^{125}$I labeled monoclonal antibodies in a modification of the procedure of Chapman, M.D., et al. (supra). Polyvinylchloride microtiter plates were coated with 1 ug/well of the monoclonal antibody 3F4 in 0.1M bicarbonate buffer, pH 9.6 overnight at 4° C., and residual binding sites were blocked with 0.1 ml 1% bovine serum albumin (BSA) in phosphate-buffered saline, pH 7.2, containing 0.05% Tween 20 (1% BSA PBS-T). Each well was incubated with 0.1 ml of a 200 ug/ml solubilized amoebic membrane fraction for 2 hr, washed 5× with PBS-T, and then incubated with cold test mAb, together with 2.5 ng of $^{125}$I labeled competing mAb for 4 hr. After further washing, the plates were dried, and individual wells were counted in a gamma counter. (For assays using $^{125}$I 3F4, lectin was directly bound to microtiter wells or coupled to the solid phase using 1 ug/well 7F4.) All assays were carried out in duplicate and the sample diluent was 1% BSA PBS-T.

Uninhibited binding of $^{125}$I to lectin was calculated from the mean cpm of four wells incubated with PBS-T. The percent inhibition of each of six labeled mAb by different cold mAb was calculated as the difference between the mean cpm of the control and the mean cpm of wells treated with cold mAb divided by the mean cpm of control (times 100). Thus, the diminution in the binding of the labeled antibody caused by the presence of the cold mAb was used as the basis for calculation.

In all cases, the binding of radiolabeled antibody was inhibited 94–98% by the same cold mAb; mAb from other clones if binding to other epitopes, generally inhibited binding by less than 20%. These results show that the six designated monoclonal antibodies bind to six different epitopes.

When all ten mAbs were tested, it was found that:

Epitope 1 was recognized by four mAbs; 3F4, 4F4, 3H6 and 5B8, all IgG1 isotypes; the mAb 3F4 was deposited with the American Type Culture Collection (ATCC), Rockville, Md., under the conditions of the Budapest Treaty on Feb. 15, 1990, ATCC HB10359;

Epitope 2 was recognized by one mAb, 8A3 isotype IgG1; the mAb 8A3 was deposited at ATCC under the conditions of the Budapest Treaty on Feb. 15, 1990, ATCC HB10357;

Epitope 3 was recognized by the mAb designated 7F4, isotype IgG2B; the mAb 7F4 was deposited at ATCC under the conditions of the Budapest Treaty on Feb. 15, 1990, ATCC HB10358;

Epitope 4 was recognized by mAb 8C12 and 6H3, also both IgG1 isotypes;

Epitope 5 was recognized by mAb 1G7 (IgG2B); and

Epitope 6 was recognized by mAb H85 (IgG2B).

Cross-inhibition studies using immune sera from human patients with liver abscess showed that these immune sera blocked the binding of monoclonal antibodies to all six epitopes.

B. In a manner similar to that set forth in paragraph A of this example, the monoclonal antibody preparations obtained from animals immunized with the nonpathogenic-derived 170 kd subunit are assayed for epitope specificity by cross-inhibition in RIA assay. A series of epitopes is obtained, including epitopes corresponding to epitopes 1 and 2 of the pathogenic strain, with which the nonpathogenic antibodies are cross-reactive.

EXAMPLE 3

Sorting of Pathogenic/Nonpathogenic Binding Epitopes

The pathogenic strain HMI-IMSS was cultured as described above. In addition, both pathogenic and nonpathogenic strains were grown in nonaxenized cultures in TYSGM-9 medium containing rice starch in the presence of bacterial flora; some nonpathogenic amoebae were grown in Robinson's media or TYI-S33 containing bacterial associates.

Some amoebae were washed in 75 mM Tris, 65 mM NaCl pH 7.5, pelleted and lyophilized for transport to the US when necessary. The strains were classified into pathogenic and nonpathogenic zymodemes by thin layer starch electrophoresis followed by visualization of the hexokinase and phosphoglucomutase isoenzyme bands as described by Sargeaunt, P. G., et al., *Trans R Soc Trop Med Hyg* (1978) 72:519–522.

The specificity of the various mAb described in Example 2 for pathogenic or nonpathogenic strains was tested as follows: polyvinyl chloride microtiter plates were coated with the 3F4 mAb, which binds to epitope 1, and blocked as described in Example 2. Serial dilutions of solubilized amoebae prepared as above were added to the wells and incubated for 2–4 hours at room temperature. The plates were then washed and $1.2\times10^5$ cpm of $^{125}$I labeled monoclonal antibody identified as specific for one of the epitopes 2–6 were added for an additional 2–4 hours incubation period. After further washing, the plates were dried and individual wells were counted in a gamma counter. As controls, standard curves using a plate assay with lectin as described in Preparation 2 were performed for each tested antibody and the results were expressed as picograms lectin detected/$10^3$ amoebae.

The RIA performed as described above is capable of detecting as few as 30 pathogenic strain HMI-IMSS amoebae or 0.5 nanograms of antigen in a well. When the nonpathogenic zymodeme CDC:0784:4 was used as the test organism, no antigen could be detected even with 1,000 amoebae/well, using the epitope 3 mAb 7F4 as the detecting reagent.

FIG. 1 shows the results of the RIA performed as described with epitope 1 mAb as capture antibody and epitope 3 mAb as detection antibody on a panel of 18 pathogenic and 32 nonpathogenic zymodemes. As shown in FIG. 1, there is a complete correlation between pathogenicity and response in the test. Those pathogens which gave weaker results were those lyophilized and sent from South Africa to the United States, so that this could be due to instability of the lectin.

when the RIA was modified so that the epitope 2 antibody 8A3 was used as a detection antibody (the antibody to epitope 1 remains as the capture antibody), a similar sensitivity was found for pathogens. FIG. 2 shows the results of this assay when the same panel of pathogenic and nonpathogenic amoebae were subjected to this assay. As shown in FIG. 2, apparently the mAb to epitope 2 reacts with both pathogenic and nonpathogenic strains. The presence of a 170 kd antigen in the membranes of nonpathogenic strains was confirmed by Western blot.

Similar experiments varying the epitope recognition characteristic of the detection antibody showed that epitopes 1 and 2 are apparently shared by both pathogenic and nonpathogenic strains, whereas epitopes 3-6 are apparently unique to pathogenic forms.

The effects of antibodies recognizing these epitopes on adherence to erythrocytes, human colonic mucins, and Chinese hamster ovary cells, were also tested. It was found that monoclonal antibodies to epitopes 1 and 2 in fact enhanced the adherence of the amoebic trophozoites in vitro; only the antibodies immunoreactive with epitopes 4–6 inhibited this adherence. The results for all of the foregoing are summarized in Table 1.

TABLE 1

| | | | Zymodeme | | |
|---|---|---|---|---|---|
| Epitope | mAb | IgG Isotype | Pathogenic[1] | Non-pathogenic[2] | mAb Effect on Adherence[3] |
| 1 | 3F4 | 1 | + | + | enhance |
| 2 | 8A3 | 1 | + | + | enhance |
| 3 | 7F4 | 2B | + | − | none |
| 4 | 8C12 | 1 | + | − | inhibit |
| 5 | 1G7 | 2B | + | − | inhibit |
| 6 | H85 | 2B | + | − | inhibit |

1. 16 isolates tested
2. 27 isolates tested
3. Adherence of pathogenic strains to human colonic mucins and Chinese Hamster ovary cells (W. A. Petri, Jr., et al., submitted)

Similar patterns of mAb binding were found for the mAbs prepared to be immunospecific for the 170 kd subunit of the nonpathogenic forms. The mAbs immunoreactive with epitope 1 and 2 are similarly immunoreactive with epitopes 1 and 2 of the pathogenic strains and are thus cross-reactive with mAbs reactive with these pathogenic epitopes.

EXAMPLE 4

Diagnostic Assay

Stool samples from suspected carriers of *E. histolytica* are prepared and worked up using standard procedures such as those described in the studies of stool specimens summarized in *Amebiasis: Human Infection by Entamoeba Histolytica*, J. Ravdin, ed., cited above. The resulting samples are then used for assay, The samples are first treated to solubilize the Gal/-GalNAc lectin by treatment with solubilization buffer of 150 mM NaCl, 50 mM Tris, pH 8.3, 0.5% nonidet P40, 5 mM EDTA and 2 mM phenylmethyl sulfonyl fluoride. The solubilized amoebae are then microfuged for 10 minutes and the supernatant recovered.

Microtiter plates are coated with the 3F4 antibody immunoreactive with epitope 1. Epitopes immunoreactive with this epitope, especially 3F4, ATCC HB10359, are preferred for use as capture antibodies because of their ability to bind both the solid support and the antigen with a higher affinity than other mAbs which bind to epitopes common to pathogenic and nonpathogenic forms. The plates are then blocked as described in Example 2. Serial dilutions of the solubilized amoebae from the samples, prepared as described above, are added to the wells and the wells are incubated for 2–4 hours at room temperature. The plates are then washed and treated with a detection antibody comprising either 8A3, ATCC HB10357, if all *E. histolytica* regardless of pathogenicity are to be detected or 7F4, ATCC HB10358, if only pathogenic strains are to be detected, or an antibody prepared as in Example 3 binding uniquely with a nonpathogenic epitope if nonpathogens are to be detected. These detection antibodies are labeled with 125-I or with alkaline phosphatase, depending on whether RIA or ELISA is to be used. The plates are again incubated for 4 hours, and then washed. Binding of detecting antibody is determined in a gamma counter for radiolabeled detection antibody and using a substrate solution according to standard procedures for the detection of alkaline phosphatase, if the enzyme labeled assay is to be used.

Samples containing pathogens give positive results when the detection antibody is either 8A3 or 7F4; samples containing nonpathogenic strains give positive results with nonpathogenic specific detecting antibodies and with 8A3. Uninfected samples are negative in all versions of the assay.

We claim:

1. A monoclonal antibody that specifically binds to an epitope which is unique to the 170 kd subunit of the Gal/GalNAc lectin of pathogenic *E. histolytica.*

2. The monoclonal antibody of claim 1 that binds to the same epitope as monoclonal antibody 7F4 produced by hybridoma ATCC HB10358.

3. A monoclonal antibody that specifically binds to an epitope which is shared by to the 170 kd subunit of the Gal/GalNAc lectin of pathogenic and nonpathogenic *E. histolytica.*

4. The monoclonal antibody of claim 3 that binds to the same epitope as monoclonal antibody 3F4 produced by hybridoma ATCC HB10359.

5. The monoclonal antibody of claim 3 that binds to the same epitope as monoclonal antibody 8A3 produced by hybridoma ATCC HB 10357.

* * * * *

UNITED STATES PATENT AND TRADEMARK OFFICE
CERTIFICATE OF CORRECTION

PATENT NO. : 5,401,831
DATED : March 28, 1995
INVENTOR(S) : PETRI et al.

It is certified that error appears in the above-indentified patent and that said Letters Patent is hereby corrected as shown below:

On the title page, item [57], delete "70 kd subunit" and insert --"170 kd subunit--.

Signed and Sealed this

Twenty-fifth Day of July, 1995

Attest:

BRUCE LEHMAN

Attesting Officer

Commissioner of Patents and Trademarks